United States Patent
Okutsu et al.

(12)
(10) Patent No.: US 6,495,703 B1
(45) Date of Patent: Dec. 17, 2002

(54) PROCESS FOR THE PREPARATION OF GLYCEROL CARBONATE

(75) Inventors: Munehisa Okutsu, Wakayama (JP); Tomohito Kitsuki, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/913,719

(22) PCT Filed: Feb. 24, 2000

(86) PCT No.: PCT/JP00/01072

§ 371 (c)(1),
(2), (4) Date: Aug. 17, 2001

(87) PCT Pub. No.: WO00/50415

PCT Pub. Date: Aug. 31, 2000

(30) Foreign Application Priority Data

Feb. 24, 1999 (JP) .......................................... 11-046103

(51) Int. Cl.⁷ ...................... C07D 317/20; C07D 301/02
(52) U.S. Cl. ........................................ 549/229; 549/518
(58) Field of Search ................................. 549/229, 518

(56) References Cited

U.S. PATENT DOCUMENTS

| 5,359,094 A | | 10/1994 | Teles et al. .................. 549/228 |
| 6,025,504 A | * | 2/2000 | Claude et al. ............... 549/229 |

FOREIGN PATENT DOCUMENTS

| EP | 0 443 758 | 8/1991 |
| EP | 0 581 131 | 2/1994 |
| EP | 0 739 888 | 10/1996 |
| EP | 0 955 298 | 11/1999 |
| JP | 6-157509 | 6/1994 |

OTHER PUBLICATIONS

Patent Abstracts of Japan, JP 60–100571, Jun. 4, 1985.

* cited by examiner

*Primary Examiner*—Bernard Dentz
(74) *Attorney, Agent, or Firm*—Oblon, Spivak, McClelland, Maier & Neustadt, P.C.

(57) ABSTRACT

The present invention provides a simple and inexpensive process for preparing glycerol carbonate. Namely, according to the present invention, glycerol carbonate is prepared by reacting glycerol with urea.

15 Claims, No Drawings

PROCESS FOR THE PREPARATION OF GLYCEROL CARBONATE

This application is a 371 of PCT/JP00/01072 filed Feb. 24, 2000.

TECHNICAL FIELD

The present invention relates to an inexpensive process for preparing glycerol carbonate.

Glycerol carbonate is applied to use in various fields, e.g. raw materials for synthesis of polymers such as polyester, polycarbonate, polyurethane and polyamide, surfactants and lubricating oils. For example, German Patent No. 19756454 discloses application to an emulsifier for cosmetics and a lustering agent. Furthermore it is shown in U.S. Pat. No. 2,856,413 that it can be easily converted to glycidol.

BACKGROUND ARTS

A reaction thereof with phosgene and an exchange reaction with a dialkyl carbonate are known as a conventional method of preparing glycerol carbonate from glycerol. A method of reacting glycerol with carbon monoxide and oxygen at a high pressure in the presence of a catalyst is also known in JP-A 6-157509, corresponding to U.S. Pat. No. 5,359,094. A less expensive, simpler method using a highly safe material, however, has been desired. It has been therefore asked to conduct the reaction with a catalyst easily treated or without catalyst.

DISCLOSURE OF INVENTION

The purpose of the present invention is to provide a process for preparing glycerol carbonate simply at a low cost.

The present inventors have found that glycerol carbonate can be synthesized by reaction of glycerol with urea.

The present invention provides a process for preparing glycerol carbonate by reaction of glycerol with urea.

More specifically, the invention provides a process for preparing glycerol carbonate, comprising reacting glycerol with urea in the presence of a metal oxide catalyst or in the absence of any catalyst.

The reaction is preferably carried out in the presence of a dehydrating agent.

It is preferable to feed urea in a 0.2 to 2.0 times as many moles as glycerol.

The reaction may be preferably carried out in the presence of anhydrous magnesium sulfate, anhydrous sodium sulfate, anhydrous calcium sulfate or a molecular sieve.

The catalyst is desirably used in an amount of 0.001 to 10 wt % based on glycerol.

The reaction is preferably conducted at a temperature between 100° C. and 140° C., more preferably at a temperature between 100° C. and 120° C., in particular preferably at a temperature between 110° C. and 120° C.

WORKING EMBODIMENTS OF INVENTION

In the present process comparatively inexpensive glycerol and urea are used as starting materials. Glycerol carbonate can be easily produced just by reacting them with each other. The feeding mole ratio of urea to glycerol may be preferably 0.2 to 2.0, particularly 0.5 to 1.0.

The invention reaction does not essentially need a catalyst. The reaction proceeds smoothly by using as catalyst a metal oxide such as zinc oxide and an alkaline earth metal oxide, e.g. magnesium oxide. A preferred amount of the used catalyst is 0.001 to 10 wt % based on glycerol.

In the present process, it is desirable to use a sufficiently dehydrated glycerol. In the reaction dehydrating agents such as anhydrous magnesium sulfate, anhydrous calcium sulfate, anhydrous sodium sulfate and molecular sieve may be preferably used. The reaction may be conducted preferably in passing of nitrogen gas or at a reduced pressure in order to remove out generated ammonia efficiently. The passing amount of nitrogen gas is not specified as long as ammonia and excess water can be removed. Nitrogen gas may be preferably introduced into the glycerol liquid phase. The reaction may be conducted at a reduced pressure, for example, in the range of 13.3 to 101 kPa.

A preferred reaction temperature ranges from 80° to 160° C., more preferably from 100° to 140° C. and particularly preferably from 110° to 120° C.

According to the present process, comparatively inexpensive materials can be used. No high pressure equipment is not required. Glycerol carbonate can be prepared simply. Glycerol carbonate obtained by the present process can be easily converted to glycidol by known means.

EXAMPLES

Example 1

92 g of glycerol was fed in a flask. It was heated up to 120° C. in passing of nitrogen gas and then was stirred for two hours. It was cooled down to 80° C. Then 60 g of urea was dissolved therein and 10 g of anhydrous magnesium sulfate was added thereto. The mixture was heated up to 120° to 140° C. and allowed to stand as it was for reaction over 6 hours. It was found in gas chromatographic analysis that a glycerol conversion was 72% and a selectivity of glycerol carbonate was 92%.

Example 2

92 g of glycerol was fed in a flask. It was heated up to 120° C. in passing of nitrogen gas and then was stirred for two hours. It was cooled down to 80° C. Then 60 g of urea was dissolved therein and 7.0 g of zinc oxide was added thereto. The mixture was heated up to 120° C. and allowed to stand as it was for reaction over 6 hours. It was found in gas chromatographic analysis that a glycerol conversion was 62% and a selectivity of glycerol carbonate was 93%.

Example 3

92 g of glycerol and 7.0 g of anhydrous magnesium sulfate were introduced into a flask. They were heated up to 120° C. in passing of nitrogen gas and stirred for two hours. They were cooled down to 80° C. Then 60 g of urea was dissolved therein and 7.0 g of zinc oxide was added thereto. The mixture was gradually heated to 120° C. and allowed to stand as it was for reaction over 6 hours. It was found in gas chromatographic analysis that a glycerol conversion was 64% and a selectivity of glycerol carbonate was 92%.

Reference Example 100 g of glycerol carbonate obtained in Example 1 was fed in a flask. 10 g of sodium sulfate was added thereto. The mixture was heated up to 200° to 210° C. at the reduced pressure of 3.33 kPa, while stirred. In the meanwhile glycidol being produced together with carbon dioxide was recovered in the form of 53.5 g of the distillate (approximate yield 85%). In gas chromatographic analysis the glycidol was found to have a purity of 90% and contain 10% of glycerol carbonate being the starting material. The selectivity of glycidol was 99% or higher.

What is claimed is:

1. A process for preparing glycerol carbonate that comprises:

reacting glycerol with urea in the presence of a metal oxide catalyst, wherein said metal oxide catalyst is zinc oxide.

2. The process according to claim 1, wherein urea is fed in an amount of 0.2 to 2.0 times as many moles as glycerol.

3. The process according to claim 1, wherein urea is fed in an amount of 0.5 to 1.0 times as many moles as glycerol.

4. The process according to claim 1 that is conducted at reduced pressure in the range of 13.3 to 101 kPa.

5. The process according to claim 1, wherein the catalyst is used in an amount of 0.001 to 10% by weight to glycerol.

6. The process according to claim 1, wherein the reaction is conducted at a temperature between 100° C. and 140° C.

7. The process according to claim 1, wherein the reaction is conducted at a temperature between 100° C. and 120° C.

8. The process according to claim 1, wherein the reaction is conducted at a temperature between 110° C. and 120° C.

9. The process according to claim 1 further comprising introducing nitrogen gas for a time and under conditions suitable to remove water or ammonia.

10. The process according to claim 1 comprising reacting glycerol with urea in the presence of a dehydrating agent.

11. The process according to claim 10 that comprises:

reacting glycerol with urea in the presence of a dehydrating agent selected from the group consisting of anhydrous magnesium sulfate, anhydrous calcium sulfate, and anhydrous sodium sulfate, or in the presence of a molecular sieve.

12. The process according to claim 10, wherein the reaction is conducted at a temperature between 100° C. and 140° C.

13. The process according to claim 10, wherein the reaction is conducted at a temperature between 100° C. and 120° C.

14. The process according to claim 10, wherein the reaction is conducted at a temperature between 110° C. and 120° C.

15. A process for preparing glycidol that comprises:

reacting glycerol with urea in the presence of a metal oxide catalyst for a time and under conditions suitable for the formation of glycerol carbonate, and converting the glycerol carbonate into glycidol, wherein said metal oxide catalyst is zinc oxide.

* * * * *